United States Patent
Ross et al.

(10) Patent No.: US 7,754,155 B2
(45) Date of Patent: Jul. 13, 2010

(54) DEVICES AND METHODS FOR ISOLATING TARGET CELLS

(76) Inventors: Amelia A. Ross, 23952 Dory Dr., Laguna Niguel, CA (US) 92677; Steve Bernstein, P.O. Box 838, Los Olivos, CA (US) 93441

( * ) Notice: Subject to any disclaimer, the term of this patent is extended or adjusted under 35 U.S.C. 154(b) by 1728 days.

(21) Appl. No.: 10/246,898

(22) Filed: Sep. 18, 2002

(65) Prior Publication Data

US 2003/0175850 A1 Sep. 18, 2003

Related U.S. Application Data

(60) Provisional application No. 60/364,679, filed on Mar. 15, 2002.

(51) Int. Cl.
- *B01L 1/00* (2006.01)
- *B01L 3/00* (2006.01)
- *G01N 21/00* (2006.01)
- *G01N 33/53* (2006.01)
- *G01N 33/566* (2006.01)
- *G01N 33/567* (2006.01)
- *G01N 33/569* (2006.01)

(52) U.S. Cl. .............. 422/102; 422/52; 422/55; 422/58; 422/61; 422/73; 422/98; 422/82.01; 422/82.05; 422/100; 435/4; 435/6; 435/7.1; 435/7.2; 435/7.21; 435/7.22; 435/7.23; 435/7.24; 435/7.25; 435/173.4; 435/173.5; 435/173.7; 435/287.1; 435/287.2; 435/287.3; 435/287.6; 435/287.7; 436/164; 436/172; 436/514; 436/517; 436/518; 436/524; 356/39; 356/73; 356/315; 600/573

(58) Field of Classification Search ............ 435/4, 435/6, 173.4, 173.7, 287.6, 164, 172, 514, 435/517, 518, 524, 7.1–7.25, 173.5, 287.1–287.3; 422/52, 55, 58, 61, 73, 98, 82.01, 102, 82.05; 356/39, 73, 315; 600/573; 436/164, 172, 436/514, 517, 518, 524

See application file for complete search history.

(56) References Cited

U.S. PATENT DOCUMENTS

| | | | |
|---|---|---|---|
| 3,726,767 A | 4/1973 | White | |
| 3,745,091 A | 7/1973 | McCormick | |
| 3,904,781 A | 9/1975 | Henry | |
| 4,043,292 A * | 8/1977 | Rogers et al. | 118/667 |
| 4,391,710 A * | 7/1983 | Gordon | 210/361 |
| 4,414,197 A | 11/1983 | Dussault | |
| 4,696,743 A * | 9/1987 | Gordon et al. | 210/361 |
| 4,775,515 A * | 10/1988 | Cottingham | 422/73 |
| 4,790,640 A * | 12/1988 | Nason | 359/396 |

(Continued)

*Primary Examiner*—Unsu Jung
(74) *Attorney, Agent, or Firm*—Inskeep IP Group, Inc.

(57) ABSTRACT

A cell isolating device and method is provided to concentrate or isolate cells with specific characteristics from a mixture of different cell types. One embodiment may comprise two sub-types of antibodies that are directly conjugated to biotin ($Ab_b$) and conjugated to a fluorescent molecule ($Ab_f$). The conjugated antibodies ($Ab_b$+$Ab_f$) bind to the target cells in a mixed cell suspension. The cell suspension is then passed over an immobilized avidin or streptavidin substrate on a glass microscope slide. The biotinylated target cells adhere to the avidin/streptavidin substrate, while the unbound cells are washed off and collected in a wicking member. Captured cells on the avidin/streptavidin substrate may then be visualized directly using a fluorescent microscope or detected and enumerated via an on-board fluorescent detection device.

17 Claims, 2 Drawing Sheets

U.S. PATENT DOCUMENTS

| | | | |
|---|---|---|---|
| 4,985,206 A * | 1/1991 | Bowman et al. ............... 422/99 |
| 5,130,116 A | 7/1992 | Woo et al. |
| 5,200,151 A | 4/1993 | Long |
| 5,215,926 A | 6/1993 | Etchells, III et al. |
| 5,240,862 A | 8/1993 | Koenhen et al. |
| 5,262,334 A | 11/1993 | Berenson et al. |
| 5,356,751 A | 10/1994 | Cairncross et al. |
| 5,419,279 A * | 5/1995 | Carrico et al. ............... 118/406 |
| 5,439,649 A * | 8/1995 | Tseung et al. ................. 422/99 |
| 5,470,758 A | 11/1995 | Hayes |
| 5,506,098 A | 4/1996 | Zarling et al. |
| 5,618,731 A | 4/1997 | Stevens et al. |
| 5,695,989 A | 12/1997 | Kalamasz |
| 5,741,649 A | 4/1998 | Inazawa |
| 5,773,224 A | 6/1998 | Grandics et al. |
| 5,827,749 A | 10/1998 | Akers, Jr. |
| 5,922,615 A * | 7/1999 | Nowakowski et al. ........ 436/518 |
| 5,922,847 A | 7/1999 | Broudy et al. |
| 5,948,624 A | 9/1999 | Rothschild et al. |
| 5,951,492 A * | 9/1999 | Douglas et al. ............. 600/583 |
| 5,973,124 A | 10/1999 | Bayer et al. |
| 5,985,669 A * | 11/1999 | Palander ...................... 436/46 |
| 6,022,700 A | 2/2000 | Monks et al. |
| 6,066,448 A * | 5/2000 | Wohlstadter et al. ........... 435/6 |
| 6,143,508 A | 11/2000 | Okarma |
| 6,146,881 A * | 11/2000 | Hering .................... 435/284.1 |
| 6,162,401 A * | 12/2000 | Callaghan ................... 422/104 |
| 6,218,191 B1 * | 4/2001 | Palander ...................... 436/63 |
| 6,235,488 B1 * | 5/2001 | Tom-Moy et al. ............ 435/7.5 |
| 6,251,615 B1 | 6/2001 | Oberhardt |
| 6,319,469 B1 * | 11/2001 | Mian et al. ................... 422/64 |
| 6,365,362 B1 | 4/2002 | Terstappen et al. |
| 6,377,721 B1 | 4/2002 | Walt et al. |
| 6,426,230 B1 | 7/2002 | Feistel |
| 6,627,158 B1 * | 9/2003 | Peltier ....................... 422/100 |
| 6,673,620 B1 * | 1/2004 | Loeffler et al. ................ 436/46 |
| 2003/0175818 A1 | 9/2003 | Ross et al. |
| 2004/0266015 A1 * | 12/2004 | Favuzzi et al. ................ 436/48 |

* cited by examiner

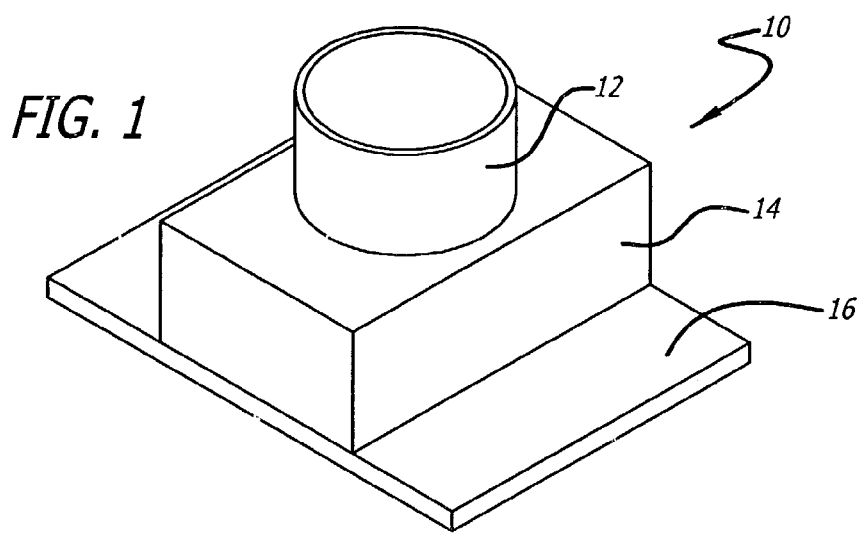
FIG. 1
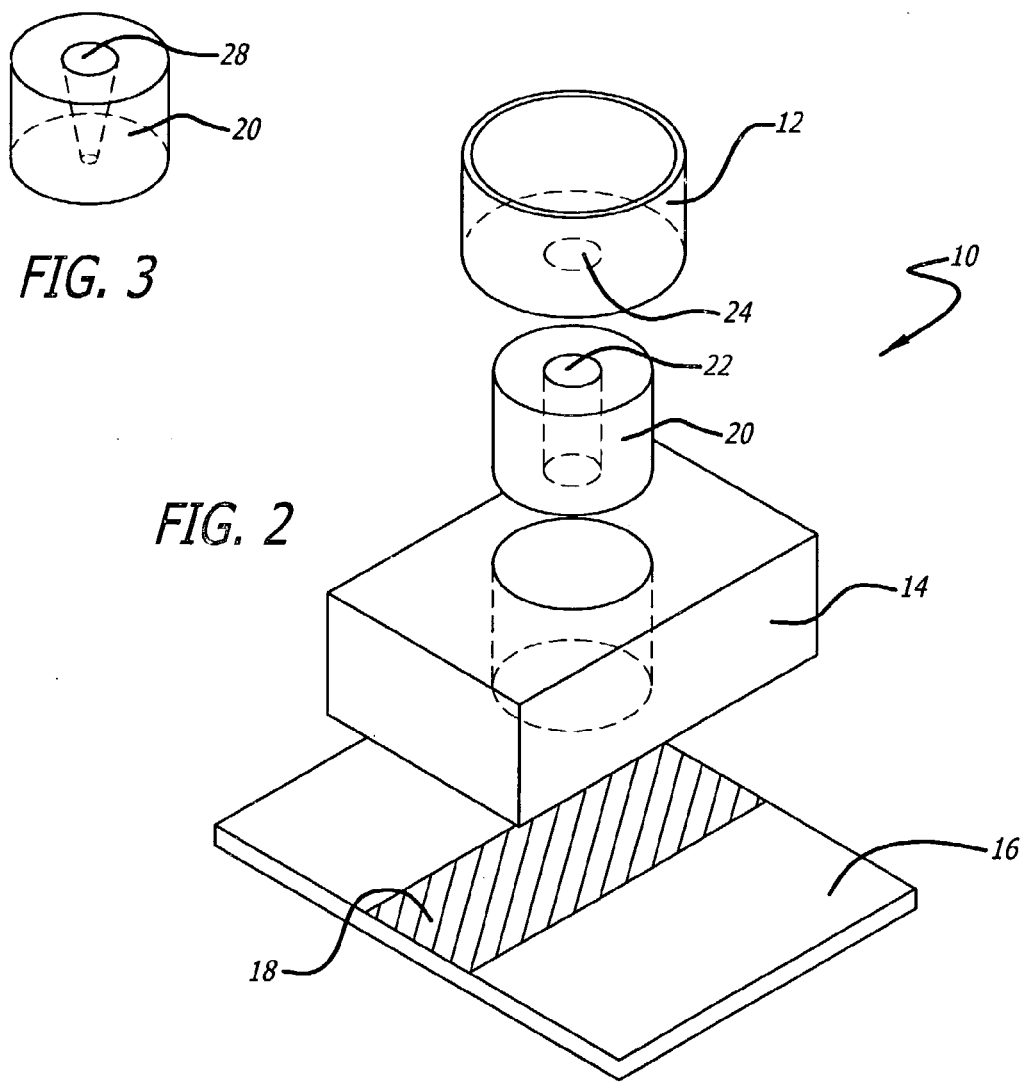
FIG. 3
FIG. 2

DEVICES AND METHODS FOR ISOLATING TARGET CELLS

CROSS REFERENCE TO RELATED APPLICATIONS

This application claims the benefit of U.S. Provisional Application No. 60/364, 679, filed Mar. 15, 2002, and whose entire contents are hereby incorporated by reference.

BACKGROUND OF THE INVENTION

All living bodies are comprised of individual cells, each cell defining an environment where various biological and chemical reactions take place. In particular, each cell contains a cell membrane that separates the internal environment of the cell from the external environment and thereby controls the entry and exit of various nutrients and waste. Additionally, the cell membrane includes various proteins, sugars, and other molecules that "identify" a particular cell type, these identifying molecules commonly being referred to as antigens.

In order to better understand the function and pathologies of cells, numerous methods have been developed to isolate and concentrate a desired target cell population from a mixed cell population so that the target cell population can be further analyzed. One such method is based upon cell density wherein a mixture of cells is spun at high speeds in a centrifuge so that the higher density cells become separated for the lesser density cells. Although this method is effective at separating different cells, centrifugation does not have good cell-separation specificity as different types of cells may have the same or similar cell density.

Accordingly, more sophisticated cell separation techniques have been developed wherein cells are separated based upon the presence of certain cellular identifiers, namely, antigens, found on the cellular membrane. More specifically, these selection methods are based upon using antibodies that react with antigens found on a particular target cell membrane. In one such method, the antibodies are affixed on the surface of a substrate, such as magnetic beads or small iron-coated particles. When mixed with the cell sample, the antibody-coated beads or particles bind to the specific antigens on the cell membrane. As a sample cell solution is passed through a magnetic separation column, the magnetic particles with the target cells attached then bind to the surface of the magnetic field. The target cells are then released from the column by removing the magnetic field from the cell separation column. Other known methods use variations of target cell binding in continuous-flow "immunoaffinity" columns. Generally, with immunoaffinity columns, once the target cells bind to the column by antigen-antibody affinity, the bound target cells are released by mechanically agitating the immunoaffinity column.

Cell separation techniques based upon cellular membrane identifiers are particularly useful in isolating specific cells as such techniques may be modified or tailored for specific target cells. Indeed, such highly specific cell separation techniques are particularly useful for diagnosing and treating specific and potent diseases such as, but not limited to, autoimmune diseases or cancer.

The utility of immunoseparation techniques as a diagnostic tool is evident given the prevalence of various diseases. Cancer, for instance, is expected to afflict approximately 1.3 million people in 2002 and result in approximately 500,000 deaths. Studies have shown, however, that early detection of cancer results in improved survival rates as treatment is more likely to be successful during the early stages of cancer. Yet while early diagnosis and treatment increases the chances of survival, there still remains the possibility of relapse. Accordingly, there has been considerable research into the causes of cancer relapse.

In particular, over the past 12 years, numerous research studies have been designed to track the presence of low numbers of micrometastic tumor cells (so called "micrometastases") in blood, bone marrow, and effusion fluids in patients with cancer. Studies have shown that the presence of tumor micrometastases in blood and bone marrow at time of surgery is a strong prognostic indicator of poor prognosis and early relapse in breast, prostate, ovarian, and lung cancer patients. Furthermore, the reappearance of circulating tumor cells following chemotherapy appears to herald the earliest indication of disease recurrence. Accordingly, the early detection of these micrometastases may result in higher survival rates for patients in relapse.

While the presence of micrometastases are strong indicators of cancer, these tumor cells are particularly difficult to detect as the reported frequency of micrometastatic tumor cells range from 1-5 micrometastatic tumor cells per 100,000-1,000,000 bone marrow cells and from 1 micrometastatic tumor cell in 1,000,000 to 100,000,000 blood cells. Despite the low frequency of micrometastases, various methods have been developed to concentrate or isolate the micrometastatic cells from blood, bone marrow, or effusion fluids using immunoselection methods such as, but not limited to, immunomagnetic separation/isolation, immunocolloidal separation/isolation, or flow cytometric separation/isolation.

While these prior art immunoselection methods have proven useful, these methods can be inefficient as they require considerable operator intervention during the separation process. For instance, the separation column usually needs cleaning and priming prior to the introduction of a sample solution. Furthermore, the column requires constant monitoring during the separation process. As a result, the efficiency, accuracy, and recovery of targeted cell is often directly related to operator skill or error. Accordingly, it is desirable to have a cell separation device that minimizes operator error.

Moreover, the design of prior art immunoseparation columns may also hinder the recovery of a targeted cell. For instance, immunomagnetic separation/isolation methods result in permanent or semi-permanent adherence of magnetic beads/particles to the isolated cells. Accordingly, the difficulty and sometimes inability to remove the target cells from the magnetic beads reduces the accuracy of these methods. For example, isolated target cells may become damaged when the cells are separated from the column as relatively harsh chemical or mechanical processes are typically required to remove the target cells from the beads. This is particularly problematic when attempting to detect cells, such as micrometastases, which have a low frequency.

Furthermore, target cell recovery is predicated on having the proper target cell to magnetic bead ratio. If the target cell to bead ratio is not properly optimized, "background" interference may develop due to the presence of beads or particles that are not bound to the target cells thereby reducing the method's accuracy. However, optimizing the target cell to bead ratio is difficult as the frequency of the target cell is usually unknown.

Accordingly, there remains a need for devices and methods that optimize target cell isolation, purity, and viability. There also remains a need for devices and methods that isolate viable, uncompromised cells (physically and/or biochemically) so as to enable subsequent analysis and potential therapeutic applications of the isolated cells.

BRIEF SUMMARY OF THE INVENTION

The present invention relates to a device and method of concentrating or isolating a target cell from a mixture having different cell types. More specifically, the target cells are isolated onto a fixed substrate through the use of a bifunctional molecule wherein a first functional group of the molecule is reactive with the fixed substrate and the second functional group is reactive with the target cell. That is, target cells may be -more easily recovered and identified because the steps of isolation and identification are carried out on the same substrate. In contrast, prior art devices and methods typically require two or more substrates to isolate and identify the target cell. In an exemplary embodiment, the present invention may be utilized in the detection of rare cellular events (e.g., tumor cells in blood, bone marrow, effusion fluids, virally infected cells, cells carrying aberrant genetic information).

According to an exemplary embodiment, the cell separating device comprises a substantially planar surface having a bioactive coating applied thereon and at least one bifunctional compound capable of binding to said target cell and to said bioactive coating. The bifunctional compound allows for the isolation of the target cell from a cellular mixture.

According to another exemplary embodiment, the cell separating device comprises a substantially planar surface having a bioactive coating applied thereon. The device further includes a conduit in spaced relationship with the planar surface, wherein the conduit includes at least one channel to deliver a cellular mixture to the bioactive coating. The device also includes a fluid absorbing media provided on the planar surface and positioned adjacent to the bioactive coating.

The present invention also provides methods of isolating a target cell from a cellular mixture. According to the teachings of the present invention, the method comprises the steps of providing a cell separation device having a planar surface coated with a bioactive coating and a bifunctional compound. The bifunctional compound is combined with the cellular mixture, and this mixture is then exposed to the bioactive coating. The bioactive coating is then analyzed for the presence of the target cell.

BRIEF DESCRIPTION OF DRAWINGS

FIG. 1 is a perspective of the cell separation device made in accordance with the teachings of the present invention;

FIG. 2 is an exploded perspective view of FIG. 1;

FIG. 3 is a perspective view of an alternate embodiment of the capillary annulus;

DETAILED DESCRIPTION OF THE INVENTION

Figure 4:
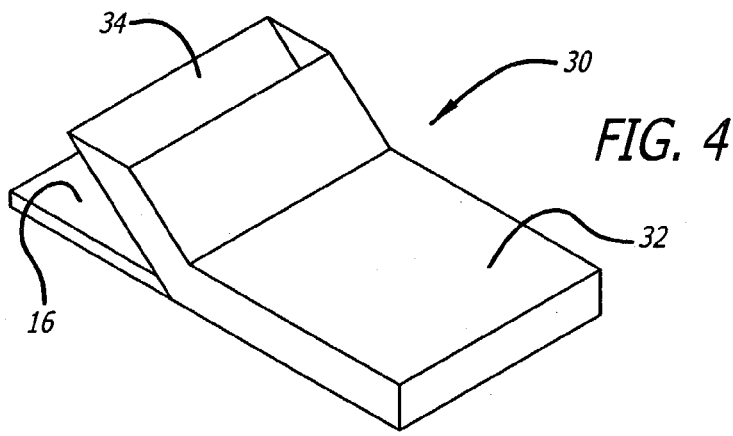
FIG. 4 is a perspective view of another exemplary embodiment of the cell separation device made in accordance with the teachings of the present invention.

The present invention relates to devices and methods of isolating and identifying a desired target cell on a single substrate. More specifically, the desired target cell is isolated from the various cells by targeting the various antigens found on the cell membrane of the target cell. That is, the present invention utilizes monoclonal antibodies that are directly conjugated to biotin and to a marker molecule wherein the conjugated antibodies are designed to bind to particular antigens found on the target cells. The present invention also utilizes the unique binding affinity of biotin (or biotin derivatives) to avidin or streptavidin to isolate the desired target cell from the cellular mixture. The target cells are separated from the cell suspension when the cell suspension is passed over an immobilized avidin or streptavidin substrate. As a result, the conjugated cells adhere to the avidin/streptavidin substrate, while the unbound cells are washed off and collected in a wicking member. The captured cells can then be reacted with other antibodies for subsequent detection and enumeration.

The device and methods are advantageous over the prior art cell separation devices. First, the present invention optimizes target cell recovery and purity as the captured target cell may be easily identified and separated from the substrate. Rather, unlike prior art devices that utilize spherical beads, the present invention utilizes a planar substrate where the target cell may be separated from a cell mixture and may also be identified on the substrate. Consequently, the isolated cells may easily be identified on a planar surface as compared to a spherical bead. Moreover, the present invention also eliminates the steps of removing the target cell from the substrate for subsequent identification. Rapid identification and capture of a specific target cell is particularly important where the target cell, such as micrometastases, has a very low frequency. Nevertheless, the devices and methods of the present invention are also useful for identifying and capturing target cells that have a lower or greater frequency than micrometastases.

According to an exemplary embodiment of the present invention, the cell separation apparatus 10 comprises a fixed substrate 16 such as, but not limited to, a standard glass microscope slide. The fixed substrate 16 may be made from materials such as, but not limited to, metal, glass, plastic, or ceramic materials. As shown in FIG. 2, the fixed substrate 16 is provided with a bioactive coating 18 applied to a defined area that may have a plurality of shapes such as, but not limited to, a circle, an oval, a square, or a rectangle. According to exemplary embodiments of the present invention, the bioactive coating 18 may be avidin, streptavidin, or derivatives thereof. For purposes of example, but not of limitation, the bioactive coatings will be referred to as "avidin" coating.

The avidin coating 18 may be applied to the fixed substrate 16 by a number of methods. One method includes directly bonding avidin 18 to the fixed substrate's surface. By directly attaching the avidin to the fixed substrate 16, covalent chemical bonding techniques are required. Generally, the fixed substrate 16 must possess chemical functional groups on its surface such as carbonyl groups, primary amines, hydroxyl groups, silane groups which will form a strong, chemical bond with similar groups on the active compound. In the absence of such chemical forming functional group, techniques may be utilized to activate the material's surface before coupling the biological compound. Surface activation is a process of generating, or producing, reactive chemical functional groups using chemical or physical techniques such as, but not limited to, ionization, heating, photochemical activation, oxidizing acids, and etching with strong organic solvents.

According to an alternative method, avidin 18 is indirectly bound to the fixed substrate's surface 16 through an intermediate layer (not shown). This intermediate layer may be either covalently bound to the fixed substrate's surface or bonded through strong intermolecular attractions such as ionic or Van der Waals forces. Examples of commonly used intermediate layers include, but are not limited to, organic polymers such as silicones, polyamines, polystyrene, polyurethane, acrylates, and methoxysilanes.

As shown in FIG. 2, the capillary annulus 20 is a generally cylindrical structure having a conduit 22 that extends along the longitudinal axis of the cylindrical structure through which the cell sample may travel. The capillary annulus 20 may be made from a number of different materials such as, but not limited to, plastic, metal, or ceramic. In an alternate embodiment, the capillary annulus 20 may include a plurality of conduits that extend along the longitudinal axis. As shown in FIG. 1, the conduit 22 has a constant diameter along the length of the conduit. In an alternate embodiment, the conduit 28 may be tapered (conical) or have a decreasing radius as illustrated in FIG. 3.

The capillary annulus 20 is placed in spaced communication with the fixed substrate 16. The distance between the base of the annulus and the fixed substrate 16 is a factor in defining the flow rate of the cell sample across the avidin coated portion 18 of the fixed substrate 16. This distance is also related to the binding efficiency between the biotinlyated antibodies and the avidin as the binding efficiency is predicated on the contact time between the biotinlyated antibodies and the avidin coating. In a preferred embodiment, this distance is in the range of 2 to 20 microns.

Optionally, the capillary annulus 20 may be provided with at least one protuberance (not shown) extending axially from the edge of the base of the annulus. The protuberance(s) may be positioned along the perimeter of the annulus and is sized -so that the annulus 20 is consistently spaced a specified distance from the avidin coated area 18 of the fixed substrate. As those skilled in the art will appreciate, the protuberances may be sized differently to effect different distances between the base of the capillary annulus 20 and the surface of the fixed substrate 16. Furthermore, the capillary annulus 20 may include at least one fastening member such as, but not limited to, braces, latches, clamps, or hooks (not shown) provided about the periphery of the annulus. The fastening members serve to secure the annulus 20 to the fixed substrate 16. The fastening members are shaped to permit the attachment and removal of the annulus 20 from the substrate 16.

The cell separation device 10 may also include a specimen chamber 12 that is in communication with the capillary annulus 20. The specimen chamber 12 is a generally cylindrical chamber having at least one opening 24 provided on the bottom surface of the chamber that corresponds to the conduit opening 22 on the capillary annulus 20. In a preferred embodiment, the specimen chamber 12 is adapted to hold approximately 5.0 mL to 25.0 mL of solution. The specimen chamber 12 may be made from materials such as plastics, metals, or ceramics. As illustrated in FIGS. 1-2, the specimen chamber 12 may be reversibly attachable and detachable from the capillary annulus 20. In an alternate embodiment, those skilled in the art will appreciate that the capillary annulus 20 and the specimen chamber 12 may be made from a single piece of material.

As shown in FIGS. 1-2, a fluid absorbing media 14 surrounds the capillary annulus 20. According to one embodiment, the fluid absorbing media 14 is reversibly attached to the fixed substrate 16 by a fastening means (not shown) such as, but not limited to, braces, latches, clamps, or hooks. According to another embodiment of the present invention, the fluid absorbing media 14 may be permanently affixed to the fixed substrate 16 with glue or other bonding agents. The fluid absorbing media 14 may be comprise absorbent materials such as, but not limited to, cellulose acetate, polyester, nylon, polyolefin, or blends thereof. According to one exemplary embodiment, the fluid absorbing media 14 comprises thermal bonded extra absorbent materials supplied by Filtrona Richmond Inc. The fluid absorbing media 14 is sized to have sufficient capacity to absorb at least a volume of cells equivalent to the maximum capacity of the specimen chamber 12. Those skilled in the art will appreciate that the size and shape of the fluid absorbing media 14 may deviate from what is depicted in FIG. 1.

The fluid absorbing media 14 absorbs the unbound cells and solution that have been exposed to avidin 18 on the fixed substrate 16. Additionally, the absorptive properties of the media 14 also contribute to the binding efficiency between the biotinylated antibodies and the avidin coating. That is, the greater the absorptive properties of the media 14, the less resulting contact time between the solution and the avidin 18. Accordingly, the absorptive efficiency of the fluid absorbing media 14 must be selected so as to optimize the time for the biotinylated antibodies to bind to the avidin coating on the substrate 16.

The cell separation device of the present invention also includes at least two types of conjugated antibodies. The antibodies may be conjugated with either a biotin molecule or a marker molecule. Moreover, the antibodies are specific for the target cells and are non-reactive with the mixed cell population such as, but not limited to, blood, bone marrow, or effusion fluids. For instance, according to one embodiment of the present invention, a pan-epithelial cell antibody may be utilized. Such antibody is directed to antigens present on epithelial cell membranes. Accordingly, the cell separation device utilizing these antibodies will target and separate those cells that have antigens that react with the pan-epithelial antibody. In an alternate embodiment, antibodies that are specific to certain blood cell antigens (known as CD antigens) may be utilized. For example, CD19 and CD20 antibodies may be used to selectively capture B lymphocytes in a mixed population of blood or bone marrow cells. In yet another embodiment, antibodies to infectious agents such as, but not limited to, cytomegalovirus or HIV may also be used to selectively capture infectious cells in blood or body fluid samples.

Additionally, the present invention includes antibodies that are conjugated with marker molecules such as, but not limited to, flurochromes, radiolabels, fluorescent agents, or chromophores. The antibodies that are conjugated with a marker molecule allow the isolated target cell to be easily identified on the avidin coated slide. Accordingly, the present invention provides a device wherein cell separation and identification may occur on the same substrate.

Furthermore, according to alternate embodiments of the present invention, binder molecules, other than an antibodies, may be conjugated with biotin. The binder molecules include, but are not limited to, glycoconjugates, lectins, hormones, cell receptors, vitamins, amino acids, sugars, lipids, fatty acids, liposomes, DNA probes, or RNA probes. These binder molecules may be utilized to target particular lectins, enzymes, receptors, transport proteins, hydrophobic sites, membranes, nucleic acids, or genes.

Figure 5:
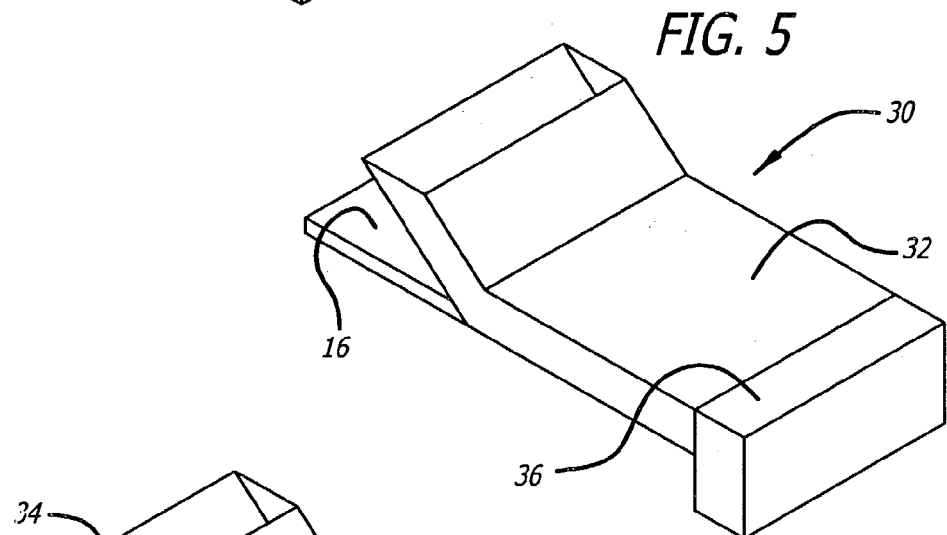
FIG. 5 is a perspective view of yet another exemplary embodiment of the cell separation device made in accordance with the teachings of the present invention.
Figure 6:
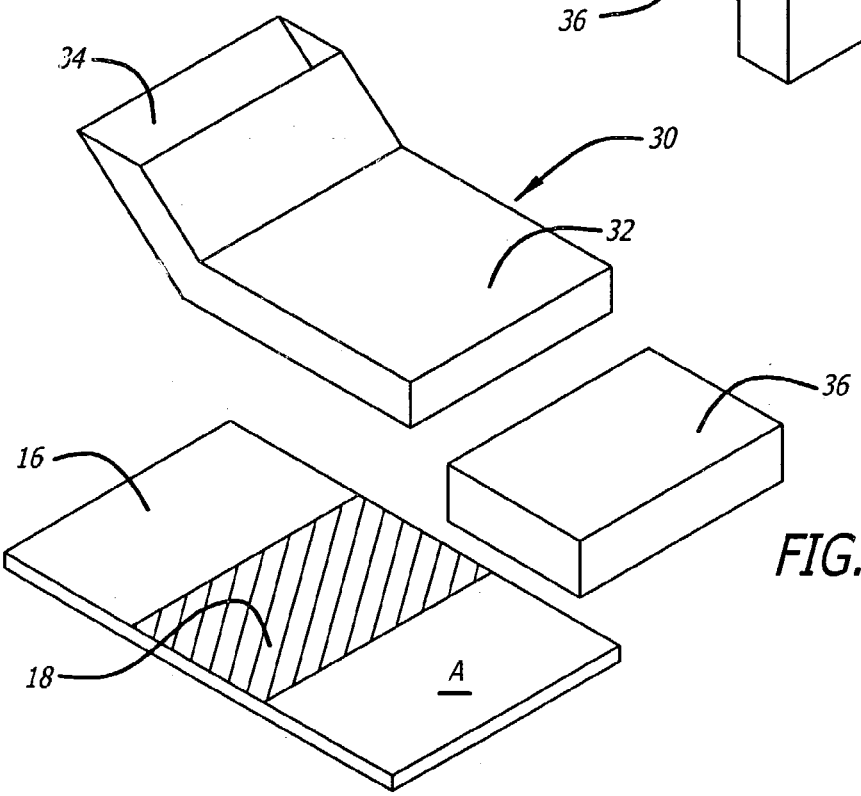
FIG. 6 is an exploded perspective view of FIG. 4.

FIGS. 4-6 illustrate other exemplary embodiments of the present invention. The cell separation device 30 comprises a fixed substrate 16 having an avidin coating 18 provided thereon, a specimen chamber 34, a capillary flow chamber 32 and a fluid absorbing media 36. Like the previous embodiment of the present invention, the avidin is provided on a defined area of the fixed substrate 16. The capillary flow chamber 32 is in communication with the fixed substrate 16 and spans at least the avidin coated region 18 of the fixed substrate 16. The capillary chamber 32 is a housing having a top wall, a first side wall, and a second side wall. The top wall is configured such that the top wall is approximately parallel to the surface of the fixed substrate 16. The first and second side walls span between the top wall and the surface of the fixed substrate 16 to define a conduit. The side walls are configured such that the capillary flow chamber 32 is reversibly attached to the fixed substrate 16 by a fastening means (not shown). The fastening means may be fasteners such as, but not limited to, braces, latches, clamps, or hooks. According to another embodiment, the capillary flow chamber 32 may be permanently affixed to the fixed substrate 16.

Generally, the specimen chamber 34 is provided at the first end of the capillary flow chamber 32 and a fluid absorbing media 36 is provided at the second end of the capillary flow chamber 32. For instance, FIG. 5 illustrates one embodiment wherein the fluid absorbing media 36 is external to the capillary flow chamber 32, and FIG. 6 illustrates a second embodiment wherein the fluid absorbing media 36 is positioned within the capillary flow chamber 32. With respect to the second embodiment as depicted in FIG. 6, the fluid absorbing media 36 is positioned downstream of the avidin coating on a surface A of the fixed substrate 16.

In operation, a cell sample is loaded into the specimen chamber. The cell sample flows across the slide, and those cells bound to biotinlyated antibodies are removed from the cell sample as the biotin reacts with the avidin. The binding between the biotin and the avidin is adjustable by varying the flow rate of the cell sample across the avidin coated portion of the fixed substrate. The flow rate may be increased by positioning the capillary flow chamber such that the specimen chamber is above the fluid absorbing media. For instance, the fixed substrate is angled such that the cell sample flows downstream towards the fluid absorbing media. Alternately, the absorptive properties of the fluid absorbing media may be increased or decreased which may increase or decrease the flow of cell sample over the avidin coating. Furthermore, a combination of the absorptive properties of the fluid absorbing media and the incline of the slide may also be adjusted to varying the flow rate of the cell sample across the avidin coated portion of the fixed substrate.

The present invention also relates to methods of isolating specific cells from a mixture of different cells. According to one method of the present invention, the cell preparation is de-bulked of red blood cells using standard laboratory procedures. The preparation is then incubated with a mixture of biotinylated antibodies [$mAb_b$] and fluorescent-conjugated antibodies [$mAb_f$]. The $mAb_b$ and the $mAb_f$ components bind to the target cells in approximate equal proportion. The cell preparation is subsequently washed to remove unbound antibodies and loaded into the specimen-loading chamber of the device. In one embodiment, the loading chamber is designed to accommodate liquid volumes ranging from approximately 5.0 ml to 25.0 ml. The cell preparation then flows through the capillary annulus at a preset flow rate that allows the $mAb_b$ on the target cell surface to bind to the avidin substrate on the slide. Cells that do not bind (non-target cells) are pulled into the absorbent wicking pad by passive absorption.

Washing fluids such as, but not limited to, phosphate buffered saline or water may be then applied into the specimen-loading chamber at a controlled flow rate. This provides for additional movement of unbound cells into the wicking pad. The specimen loading chamber, capillary annulus, and wicking pad may be then removed and the collected target cells may be viewed under a fluorescent microscope. Optionally, the slide may then be fixed with an aldehyde or cell-preservation media for permanence.

In closing, it is to be understood that the embodiments and examples of the present invention are illustrative of the principles of the present invention. Other modifications that may be employed are within the scope of the present invention; thus, by way of example, but not of limitation, alternative configurations and methods of the present invention are also contemplated. Accordingly, the present invention is not limited to that precisely shown and described herein.

What is claimed:

1. A device for isolating and identifying a target cell from a cellular mixture, said device comprising:
    a solid substantially planar surface having a bioactive coating applied on a top open planar region of said solid substantially planar surface; and,
    at least one bifunctional compound capable of binding to said target cell and to said bioactive coating; and
    a delivery conduit mounted on said solid substantially planar surface and communicating said bifunctional compound with said bioactive coating on said open planar region of said solid substantially planar surface;
    said delivery conduit mounted on said solid substantially planar surface so as to form an unsealed space between said delivery conduit and said solid substantially planar surface, said unsealed space having a predetermined height and said space allowing flow of said bifunctional compound to travel beyond said delivery conduit across said substantially planar surface over said bioactive coating on said substantially planar surface.

2. The device of claim 1 further comprising a binder molecule conjugated with a visual indicator probe.

3. The device of claim 1 wherein said bioactive coating is selected from the group consisting of avidin, streptavidin, avidin derivatives, streptavidin derivatives, and blends thereof.

4. The device of claim 1 wherein said bifunctional molecule comprises a binding molecule conjugated with a biotin molecule or a biotin derivative.

5. The device of claim 4 wherein said binding molecule is selected from the group consisting of antibodies, antigens, glycoconjugates, lectins, hormones, cell receptors, vitamins, amino acids, sugars, lipids, fatty acids, liposomes, DNA probes, and RNA probes.

6. The device of claim 2 wherein said probe is selected from the group consisting of flurochromes, radiolabels, fluorescent agents, and chromophores.

7. The device of claim 1 wherein said delivery conduit includes a capillary annulus in spaced relationship with said solid substantially planar surface.

8. The device of claim 7 further comprising a fluid absorbing media surrounding said capillary annulus.

9. The device of claim 8 further comprising a specimen chamber in communication with said capillary annulus.

10. The device of claim 1 wherein said delivery conduit includes a housing in spaced relationship with said solid substantially planar surface, said housing having an inlet located at a first end of said housing.

11. The device of claim 10 further comprising a fluid, absorbing media opposite said inlet and adjacent to said bioactive coating.

12. The device of claim 1, wherein said predetermined height of said unsealed space is in the range of approximately 2 to 20 microns.

13. The device of claim 1, further comprising at least one fastener securing said delivery conduit to said substantially planar surface.

14. The device of claim 1, wherein said substantially planar surface is a slide.

15. The device of claim 1, wherein said delivery conduit has a constant diameter.

16. The device of claim 1, wherein said delivery conduit has a tapered shape.

17. The device of claim 1, wherein said delivery conduit has a top wall and a first side wall and a second side wall.

* * * * *